(12) United States Patent
Lee et al.

(10) Patent No.: US 6,530,938 B1
(45) Date of Patent: Mar. 11, 2003

(54) CATHETER MEMBER WITH BONDABLE LAYER

(75) Inventors: Jeong Soo Lee, Diamond Bar, CA (US); Kenneth L. Wantink, Temecula, CA (US); Alan A. Tannier, Temecula, CA (US); Stephen J. Tiernan, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/458,361

(22) Filed: Dec. 9, 1999

Related U.S. Application Data

(63) Continuation of application No. 08/977,815, filed on Nov. 25, 1997, now Pat. No. 6,010,521.

(51) Int. Cl.[7] ............................................. A61M 29/00
(52) U.S. Cl. ...................................... 606/194; 606/191
(58) Field of Search ................................ 606/192, 194, 606/198, 108; 604/96–103, 104; 623/1

(56) References Cited

U.S. PATENT DOCUMENTS

| 4,003,382 A | 1/1977 | Dyke |
| 4,690,175 A | 9/1987 | Ouchi et al. |
| 4,748,982 A | * 6/1988 | Horizewski et al. .... 604/102 X |
| 4,798,597 A | 1/1989 | Vaillancourt |
| 4,994,047 A | 2/1991 | Walker et al. |
| 5,040,548 A | 8/1991 | Yock |
| 5,270,086 A | 12/1993 | Hamlin |
| 5,290,230 A | 3/1994 | Ainsworth et al. |
| 5,318,032 A | 6/1994 | Lonsbury et al. |
| 5,425,712 A | 6/1995 | Goodin |
| 5,496,275 A | 3/1996 | Sirban et al. |
| 5,499,973 A | * 3/1996 | Saab ........................... 604/96 |
| 5,538,510 A | 7/1996 | Fontirroche et al. |
| 5,545,149 A | 8/1996 | Brin et al. |
| 5,549,552 A | 8/1996 | Peters et al. |
| 5,587,125 A | 12/1996 | Roychowdhury |
| 5,669,920 A | 9/1997 | Conley et al. |
| 5,820,594 A | 10/1998 | Fontirroche et al. |
| 5,824,173 A | 10/1998 | Fontirroche et al. |
| 5,843,032 A | 12/1998 | Kastenhofer |
| 6,010,521 A | * 1/2000 | Lee et al. ..................... 606/96 |
| 6,165,166 A | 12/2000 | Samuelson et al. ......... 604/524 |

FOREIGN PATENT DOCUMENTS

| EP | 0 334 640 | 9/1989 |
| EP | 0 745 395 | 12/1996 |
| EP | 0 807 446 | 11/1997 |
| EP | 0 873 759 | 10/1998 |
| WO | WO 92/19316 | 11/1992 |
| WO | WO 97/44082 | 11/1997 |

* cited by examiner

*Primary Examiner*—Olik Chaudhuri
*Assistant Examiner*—(Vikki)Hoa B. Trinh
(74) *Attorney, Agent, or Firm*—Fulwider Patton Lee & Utecht, LLP

(57) ABSTRACT

The invention is directed to a catheter formed at least in part of a multilayered member having a first layer which is fusion bondable to another catheter component such as the skirt of an inflatable balloon and a second layer which is adjacent the first layer having a melting point greater than the first layer so that the multilayered member of the catheter is not deformed when the other catheter component is fusion bonded to the first layer of the multilayered member. The second layer is preferably lubricious in nature. In one embodiment of the invention, the multilayered member is a tubular element with the lubricious second layer defining an inner lumen extending within the tubular element. The outer layer of the tubular member may extend beyond the distal end of the inner layer and form a non-traumatic distal tip. Alternatively, a flexible non-traumatic distal tip may be fusion bonded to at least the outer layer of the multilayered tubular member.

18 Claims, 2 Drawing Sheets

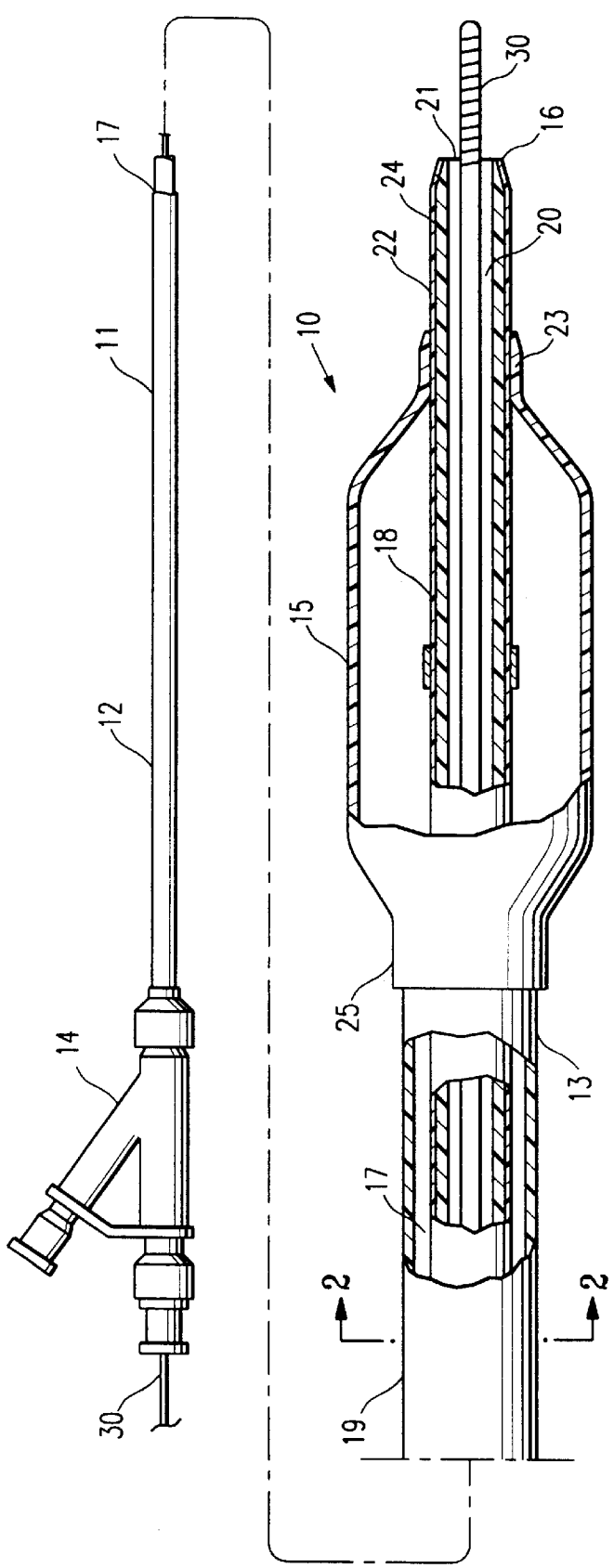
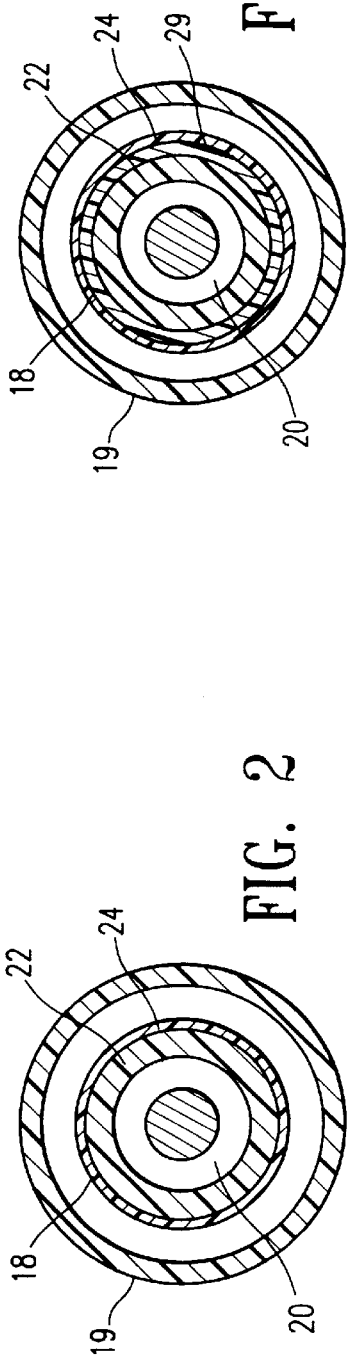
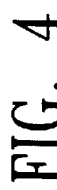
FIG. 1
FIG. 2
FIG. 4

CATHETER MEMBER WITH BONDABLE LAYER

This application is a continuation of application Ser. No 08/977,815, filed Nov. 25, 1997, now U.S. Pat. No. 6,010,521.

BACKGROUND OF THE INVENTION

This invention generally relates to intravascular catheters, particularly catheters for use in percutaneous transluminal coronary angioplasty (PCTA) or for the delivery of stents.

In a typical PTCA procedure a dilatation balloon catheter is advanced over a guidewire to a desired location within the patient's coronary anatomy where the balloon of the dilatation catheter is properly positioned within the stenosis to be dilated. The balloon is then inflated with radiopaque liquid at relatively high pressures (generally 4–12 atmospheres) to dilate the stenosed region of the diseased artery. One or more inflations may be needed to effectively dilate the stenosis. The catheter may then be withdrawn from the stenosis or advanced further into the patient's coronary anatomy to dilate additional stenoses.

In addition to the dilation of stenoses, balloon catheters similar to those described above are used to deploy stents within a patient's body lumen after a dilatation has been completed or simultaneously with the dilatation in order to maintain lumen patency. In this case an expandable stent is disposed about the exterior of the balloon on the distal extremity of the catheter and the catheter is then advanced within the patient's body lumen until the stent mounted on the exterior of the balloon is at the location in which the stent is to be deployed, e.g. usually at the stenotic site of a previous dilatation. The balloon is inflated so as to expand the stent against the wall defining the body lumen and then the balloon is deflated and the catheter withdrawn from the patient's body lumen.

Advances in the development of balloon catheters for both dilatation and stent deployment have made the selection of materials difficult because of conflicting requirements. For example, higher dilation pressures has made the sealed bonding of the balloon the catheter shaft a greater requirement, but the materials from which the high pressure balloons are made, e.g. polyethylene terephthalate, polyamide (e.g. nylon) and the like, have limited the materials to which the balloon can be bonded, and thus, the materials from which the catheter shaft can be made, particularly the distal extremity of the catheter shaft where the balloon is located.

If the distal tip of an in travascular catheter is to have non-traumatic characteristics to minimize damage when passing through a body lumen, additional material limitations come into play because typical non-traumatic tips are formed from short tubular members made of relatively soft polymeric material which are secured by adhesive or fusion bonding to the distal tip of the tubular distal extremity of the catheter.

Other complicating factors in the selection of materials for intraluminal catheters is the usual requirement that the proximal shaft be much longer and much less flexible than the distal shaft section so that the proximal shaft section provides the push to the catheter and so that the more flexible distal shaft section can be readily advanced through tortuous anatomy.

The difficulties in material selection and the more complicated construction of the more recently developed catheters make their manufacture more difficult and more expensive. What has been needed is a catheter structure which simplifies the material selection and reduces the cost of manufacture. The present invention satisfies these and other needs.

SUMMARY OF THE INVENTION

This invention is directed to an improved multilayer member for an intraluminal catheter which can be readily bonded to other catheter parts.

The multilayer member of the invention has a first layer which is fusion bondable to another catheter component and an adjacent second layer which has greater lubricity than the first layer. The first layer preferably has a melting point which is lower than the melting point of the adjacent second layer so that when the first layer is fusion bonded to another catheter component, the adjacent layer of the multilayer member is not deformed or otherwise misshapen by the heat from a bonding procedure. In a presently preferred embodiment of the invention, the multilayered member is in a tubular form with the second layer on the inside of the tubular member defining an inner lumen extending through the tubular member. The first layer which has a melting point lower than that of the second layer forms at least in part the outer layer of the tubular member.

In one aspect of the invention, the catheter has an elongated shaft with a proximal end, a distal end, a port in the distal end and a guidewire lumen extending through at least the distal portion of the catheter to and in fluid communication with the port in the distal end of the catheter shaft. In accordance with this aspect, the elongated shaft of the catheter has a multilayer tubular member with a first or outer layer which is fusion bondable to another catheter component and a second or inner layer which has lubricious properties. A high strength outer layer may be bonded to at least part of the first layer to provide additional strength and pushability. The first layer should have a melting point which is at least 20° C., preferably at least 30° C. lower than the melting point of an adjacent polymeric layer, so that the adjacent layer is not distorted by the heat from the fusion bonding procedure.

The material from which the first layer of the multilayered member, which has a lower melting point than the adjacent second layer, is selected so as to be. compatible with the polymeric material of the catheter component to which it is to be secured. A presently preferred lower melting point polymeric material is a polyolefin based copolymer with not more than 35% (by weight) reactive monomer forming the copolymer. A suitable polyolefin material is copolymerized with one or more monomers selected from the group consisting of carboxylic acid or acrylic acid or anhydride thereof and preferably is unsaturated. A presently preferred polyolefinic material is a polyethylene based adhesive polymer such as ethylene-acrylic acid copolymer which is sold commercially as PRIMACOR by Dow Chemical Co. or as ESCOR by EXXON or as PLEXAR by Quantum Chemical Corp. Other suitable materials include polymers which have been modified by reactive extrusion having a durometer range of about Shore A 80 to about Shore D 80, preferably about Shore A 90 to about Shore D 70.

The second or inkier layer of the multilayer member having lubricious properties should have a coefficient of friction (both static and dynaric) of less than 0.35 and preferably less than 0.30. Suitable polymeric materials having the aforesaid coefficient of friction include polyethylene, polytetrafluoroethylene and other fluoropolymers.

As previously mentioned a third layer may be provided on the side of the first layer opposite side in contact with the second layer and may be formed of various polymeric materials to provide a catheter shaft with additional push and to prevent collapse or kinking of the tubular member in manufacturing or use. Suitable polymeric materials for the third layer include high density polyethylene, polyethylene terephthalate (PET), polyamide, a thermoplastic polyurethane, polyetheretherketone (PEEK) and the like.

All or most of the layers of the multilayered tubular member are preferably selected or modified so that they can be melt processed, e.g. coextruded, simultaneously or sequentially, and as a result the polymeric materials of the various layers should be compatible in this regard or made compatible by appropriate additives to the polymers.

In one presently preferred embodiment of the invention, the catheter is a dilatation catheter for angioplasty or stent delivery having a balloon on a distal shaft section with a multilayered inner tubular member which extends through and distal to the balloon and which defines at least in part a guidewire lumen extending to and in fluid communication with a port in the distal end of the catheter. In this instance, the multilayered inner tubular member has a bondable outer layer and the polymeric material thereof is selected to facilitate the fusion bonding of the distal skirt of the balloon to the outer layer of the inner tubular member. The multilayered inner tubular member also has an inner layer having lubricious properties which defines at least part of the guidewire lumen.

Another embodiment of the invention is directed to an intraluminal catheter wherein the multilayered tubular member forms at least part of the shaft of the intraluminal catheter and the low melting point material of the outer bonding layer of the multilayered tubular member extends beyond an adjacent layer to form a non-traumatic distal tip on the catheter shaft.

In yet another aspect of the invention, the catheter is provided with a nontraumatic distal tip which is fusion bonded to at least the bondable layer on the multilayered tubular member. While a fusion bond somewhat limits the selection of material for the bondable layer, the preferred material discussed above, namely the polyethylene based adhesive such as PRIMACOR, ENCOR or PLEXAR facilitates fusion bonding to a wide variety of materials including polyethylene, PET, polyamide, polyurethane, PVC and copolymers such as PEBAX® and HYTREL® and the like.

In most instances the wall thickness of the fusion bondable layer of the multilayered tubular member should be less than half the wall thickness of the tubular member, preferably less than 40% of the total thickness of the member. The inner and outer dimensions of the tubular member generally follow the dimensions of other tubular members from which intravascular catheters are made.

The present invention provides an improved multilayered member which greatly facilitates bonding of one catheter component to another catheter component, particularly bonding the skirt of dilatation balloon to the inner tubular member of the catheter.

These and other advantages of the invention will become more apparent from the following detailed description of the invention when taken in conjunction with the accompanying exemplary drawings.

BRIEF DESCRIPTION OF THE DRAWINGS

FIG. 1 is an elevational schematic view, partially in section, of a dilatation catheter embodying features of the invention.

FIG. 2 is a transverse cross-sectional view of the catheter shown in FIG. 1 taken along the lines 2—2.

FIG. 4 is a transverse cross-sectional view similar to the view shown in FIG. 2 of an alternative embodiment with the inner tubular member having three layers of polymeric material.

DETAILED DESCRIPTION OF THE INVENTION

Figure 3:
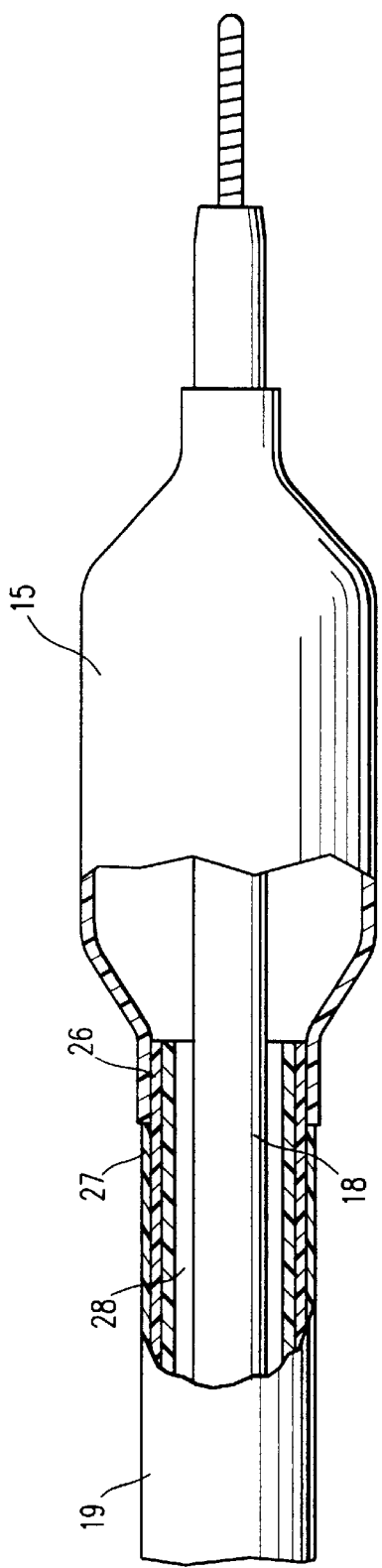
FIG. 3 is an elevational view, partially in section, of an alternative embodiment of the invention wherein a dilatation catheter has an outer tubular member with multiple layers.

Reference is made to FIGS. 1–2 which illustrate a balloon dilatation catheter 10 embodying features of the invention. Catheter 10 has an elongated shaft 11 with proximal and distal shaft sections 12 and 13, an adapter 14 on the proximal end of the shaft and a dilatation balloon 15 on the distal shaft section spaced proximal to the distal end 16. An inflation lumen 17 extends between the proximal end of shaft 11 and a location spaced proximal to the distal end 16 and is in fluid communication with the interior of the dilatation balloon 15. The catheter shaft 11 is provided with a multilayered first inner tubular member 18 and an outer tubular member or jacket 19 of suitable polymeric material or materials. A guidewire receiving lumen 20 extends through the proximal and distal shaft sections 12 and 13 to the port 21 in the distal end of the shaft 11. In the distal shaft section 13, the guidewire receiving lumen 20 is defined at least in part by the inner layer 22 of the first inner tubular member 18.

The ballon 15 has a distal skirt 23 which is secured by fusion bonding to lower melting point polymeric material of the outer layer 24 of the multilayered first inner tubular member 18 and a proximal skirt 25 which is secured by suitable means to the distal end of the outer tubular member 19 FIG. 3 illustrates an elevational view, partially in section, of an alternative embodiment in which the outer tubular member 19 defining inflation lumen 28 has multiple layers, including outer layer 27 removed from the distal portion of the outer tubular member 19 to expose the middle layer 26 for securing to the proximal skirt 25 of the balloon 15.

The multilayered tubular members of the invention may have more than two layers in other configurations. For example, as shown in FIG. 4, a high strength outer layer 29 may be provided on the exterior of low melting point bonding layer 24. While not shown in the drawings the high strength outer layer 29 may be removed from the distal portion of the inner tubular member 18 to expose the low melting point bonding layer 24. In this manner the outer layer 29 can provide strength and would still be available or bonding to the distal skirt 23 of balloon 15. As shown in FIGS. 1–4 a guidewire 30 is slidably disposed within the inner lumen 20 of the inner tubular member 18.

The multilayered tubular members described above may be readily formed by coextruding at least two of the layers thereof, and preferably all of the layers. The lubricious layer may be a hydrophilic or otherwise lubricious polymeric material which may be a homopolymer, a copolymer or a blend of polymeric materials having at least one component which develops a lubricious surface.

Figure 5:
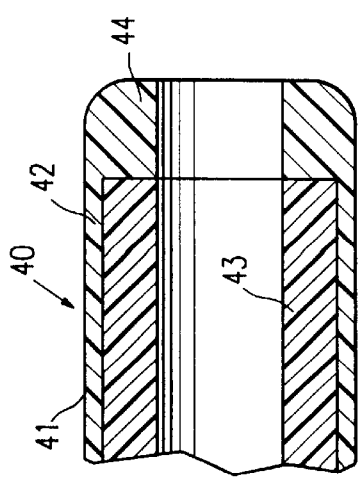
FIG. 5 is an elevational schematic view, partially in section, of the distal portion of another alternative embodiment of the invention wherein the outer layer of a tubular member of the catheter forms a non-traumatic distal tip on the catheter.

A further modification of the present invention is illustrated in FIG. 5 which depicts the distal extremity of an intravascular catheter 40 formed of a multilayered tubular member 41 wherein the outer layer 42 extends beyond the distal end of the inner layer 43 and is heat shaped so as to form a non-traumatic distal tip 44. A presently preferred method of forming the non-traumatic distal tip 44 is to heat shape the distal portion of the outer layer 42 which extends distally beyond the distal end of the inner layer 43 against the exterior of a mandrel (not shown) disposed within the guidewire lumen 45 and an exterior shaping member which heat forms the exterior of the distal tip 44.

Figure 6:
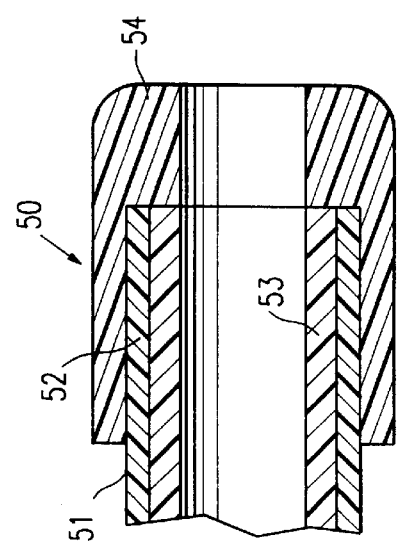
FIG. 6 is an elevational view, partially in section, of another embodiment of the invention, illustrating a non-traumatic distal tip bonded to the distal end of a multilayered inner tubular member.

FIG. 6 shows a distal extremity of an intravascular catheter 50 formed in part from a multilayered tubular member 51 having an outer layer 52 formed of bondable polymeric material as previously described, an inner layer 53 and a flexible distal tip 54 which is fusion bonded at least to the distal end or the exterior of the outer layer.

Figure 7:
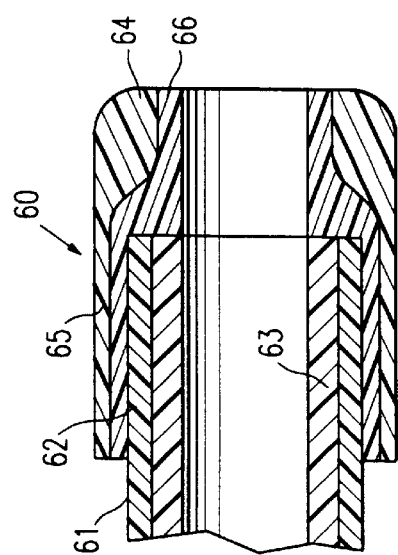
FIG. 7 is an elevational view, partially in section, of another embodiment of the invention, illustrating a non-traumatic distal tip bonded to the distal end of a multilayered inner tubular member where the non-traumatic distal tip is a multilayered tubular member.

An alternative embodiment of an intravascular catheter 60, as shown in FIG. 7, has a multilayered tubular member 61 with an outer layer 62 formed of the lower melting point polymeric material as previously described, an inner lubricious layer 63 and a flexible distal tip bonded to the end or exterior or both of the outer layer 62. The embodiment of FIG. 7 differs from that shown in FIG. 6 by having a multilayered distal tip 64 with an outer layer 65 and an inner layer 66. Preferably, the inner layer 66 is formed of a low melting point polymeric material the same as or compatible with the outer layer 62 to facilitate fusion bonding of the distal tip 64 to the exterior of the tubular member 61.

The thickness of the bonding layer generally will depend upon the material from which the layer is formed and the stresses to which the bonding layer will be exposed to in use. The dimensions of the various catheter components of the invention may generally follow the dimensions of similar components utilized in commercially available catheters. For example, for angioplasty catheters and stent delivery catheters the guidewire lumen should accommodate the guidewire having diameters of about 0.010 to 0.035 inch (0.25–0.89 mm), typically about 0.012 to about 0.018 inch (0.30–0.46 mm) so the guidewire receiving lumen should range from about 0.014 to about 0.040 inch (0.36–1.0 mm), preferably about 0.016 to about 0.023 inch (0.38–0.58 mm). If the catheter is to have perfusion capabilities, the number, size and distribution of perfusion holes in the catheter wall (not shown) is controlled to provide a perfusion flow rate of about 20–60 cc/min, preferably about 30–45 cc/min. The inflated balloon diameters may range from about 1 to about 5, typically about 2 to about 4 mm. Balloon lengths may range from about 10–50 mm, typically about 20–40 mm. The distal shaft section proximal to the balloon may range from about 0.03 to about 0.06 inch (0.76–1.52 mm), typically about 0.035 to about 0.05 inch (0.89–1.27 mm). Balloon burst pressures should be about 10 to about 20 atmospheres (147–294 psi), preferably about 12 to about 15 atmospheres (176–221 psi). To extent not described herein dimensions and materials described in the references incorporated herein and dimensions and materials used in commercially available dilatation and stent delivery catheters may be employed with the catheters of the present inventions.

The catheter of the invention may be of a rapid exchange type catheter such as described in U.S. Pat. No. 5,040,548 (Yock), U.S. Pat. No. 4,748,982 (Horzewski et al.), U.S. Pat. No. 5,496,275 (Sirhan et al) and U.S. application Ser. No. 08/484,267, filed on Jun. 7, 1995, which have been incorporated herein. In these catheters the guidewire lumen extends from a distal port in the distal end of the catheter shaft to a proximal port spaced proximally about 7 to about 45 cm, preferably about 15 to about 35 cm, from the distal end of the catheter shaft.

Although individual features of embodiments of the invention may be shown in some of the drawings and not in others, those skilled in the art will recognize that individual features of one embodiment of the invention can be combined with any or all the features of another embodiment. Moreover, various modifications can be made to the present invention without departing from the scope thereof.

What is claimed is:

1. An intraluminal catheter, comprising:
   a) a first catheter part comprising a multilayered tubular member having an inner layer formed of a lubricious polymeric material a low melting point middle layer formed of an adhesive polymer with a melting point lower than a melting point of the inner layer polymeric material, and an adjacent polymeric layer which is bonded to an outer surface of the middle layer and which forms an outer layer; and
   b) a second catheter part having at least a section bonded to a distal section of the middle layer of the multilayered tubular member.

2. The catheter of claim 1 wherein the adhesive polymer comprises a polyolefin based copolymer formed from a polyolefin with up to about 35% by weight of a comonomer having reactive groups.

3. The catheter of claim 1 wherein the adhesive polymer comprises a polyethylene based adhesive polymer.

4. The catheter of claim 2 wherein the comonomer is selected from the group consisting of carboxylic acid, acrylic acid, maleic acid, and anhydrides thereof.

5. The catheter of claim 1 wherein the middle layer of the multilayered tubular member is formed of an ethylene-acrylic acid copolymer.

6. The catheter of claim 1 wherein the outer layer of the multilayered tubular member is formed of a material selected from the group consisting of polyethylene, polyethylene terephthalate, polyamide, thermoplastic polyurethane, and polyetheretherketone.

7. The catheter of claim 1 wherein the inner layer of the multilayered tubular member has a static coefficient of friction of less than about 0.35.

8. The catheter of claim 1 wherein the inner layer of the multilayered tubular member has a static coefficient of friction of less than about 0.30.

9. The catheter of claim 1 wherein the inner layer of the multilayered tubular member is thicker than the outer layer.

10. The catheter of claim 1 wherein the outer layer of the multilayered tubular member is thinner than the middle layer.

11. The catheter of claim 1 wherein the middle layer of the multilayered tubular member is thinner than the inner layer.

12. The catheter of claim 1 wherein the second catheter part is a skirt of a balloon.

13. The catheter of claim 1 wherein the second catheter part is formed of a material selected from the group consisting of polyolefin, polyester, polyamide and copolymers thereof.

14. The intraluminal catheter of claim 1 further comprising a third catheter part having at least a section bonded to a distal section of the outer layer of the multilayered tubular member.

15. An intraluminal catheter, comprising:

a) an elongated shaft formed at least in part by a multilayered tubular member which at least in part defines a guidewire lumen, the multilayered tubular member having an inner layer informed of a lubricious polymeric material, a middle layer formed of an adhesive polymer with a melting point lower than a melting point of the inner layer polymeric material, and an adjacent polymeric layer which is bonded to an outer surface of the middle layer and which forms an outer layer; and b) a non-traumatic distal tip on a distal end of the shaft formed by a tubular member having an outer layer and an inner layer which is secured to the middle layer of the multilayered tubular member or the distal end thereof.

16. The intraluminal catheter of claim 15 further comprising a balloon having at least a section bonded to a distal section of the outer layer of the multilayered tubular member.

17. An intraluminal catheter, comprising:

a) a first catheter part comprising a multilayered tubular member having an inner layer formed of a lubricious polymeric material, a middle layer formed of an adhesive polymer with a melting point lower than a melting point of the inner layer polymeric material, and an adjacent polymeric layer which is bonded to an outer surface of the middle layer, and which forms an outer layer which has a thickness less than a thickness of the middle layer; and b) a second catheter part having at least a section bonded to a distal section of the middle layer of the multilayered tubular member.

18. The intraluminal catheter of claim 17 wherein the outer layer thickness is less than a thickness of the inner layer.

* * * * *

UNITED STATES PATENT AND TRADEMARK OFFICE
CERTIFICATE OF CORRECTION

PATENT NO. : 6,530,938 B1  Page 1 of 1
DATED : March 11, 2003
INVENTOR(S) : Jeong Soo Lee et al.

It is certified that error appears in the above-identified patent and that said Letters Patent is hereby corrected as shown below:

Title page,
Item [56], U.S. PATENT DOCUMENTS, add:
-- 5,989,218   11/1999   Vasicek --.

Column 4,
Line 48, after "19", add -- . -- and two spaces.

Column 6,
Line 20, after "material", add -- , --.
Line 30, after "polyolefin", add -- polymerized --.

Signed and Sealed this

Second Day of September, 2003

JAMES E. ROGAN
*Director of the United States Patent and Trademark Office*